Figure 1A:
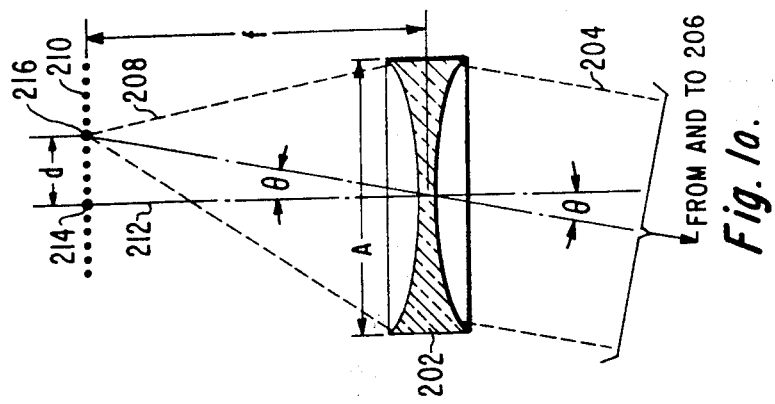

United States Patent [19]

Mezrich et al.

[11] 4,131,024
[45] Dec. 26, 1978

[54] PULSE-ECHO ULTRASONIC-IMAGING DISPLAY SYSTEM

[75] Inventors: Reuben S. Mezrich, Rocky Hill; David H. R. Vilkomerson, Princeton, both of N.J.

[73] Assignee: RCA Corporation, New York, N.Y.

[21] Appl. No.: 766,528

[22] Filed: Feb. 7, 1977

[30] Foreign Application Priority Data

Mar. 4, 1976 [GB] United Kingdom ............... 08663/76

[51] Int. Cl.² ............................................. G01N 29/00
[52] U.S. Cl. ........................................ 73/606; 73/626
[58] Field of Search ............... 73/67.5 R, 67.7, 67.8 R, 73/67.8 S, 67.9, 71.5 US, 606, 607, 625, 614, 632, 626, 641, 642, 629; 340/5 MP, 5 H, 8 FT; 128/2 V, 2.052

[56] References Cited

U.S. PATENT DOCUMENTS

| | | | |
|---|---|---|---|
| 2,833,999 | 5/1958 | Howry | 73/642 |
| 3,794,964 | 2/1974 | Katakura | 340/5 MP |
| 3,886,490 | 5/1975 | Green | 340/5 MP |
| 3,895,525 | 7/1975 | Eichelberger et al. | 340/5 MP |
| 3,918,024 | 11/1975 | Macovski | 340/5 MP |
| 3,918,297 | 11/1975 | Rocha | 73/607 |
| 3,937,066 | 2/1976 | Green et al. | 340/5 MP |
| 4,016,750 | 4/1977 | Green | 73/629 |

*Primary Examiner*—Stephen A. Kreitman
*Attorney, Agent, or Firm*—H. Christoffersen; Samuel Cohen; George J. Seligsohn

[57] ABSTRACT

An improved pulse-echo ultrasonic-imaging system for scanning, in real time, objects such as soft tissue within a living human body. It employs a transducer including first and second parallel wave-energy generating electrodes extending linearly in a first direction and a linear array of image-spot detecting electrodes also extending in this first direction and is situated half-way between the first and second electrodes. Scanning in a second direction orthogonal to the first direction is provided by counter-rotating Risley prisms rotating at a predetermined rate. The distance between each of the first and second electrodes and the linear array is related to this predetermined rate such that reflected wave energy is always directed to the linear array.

3 Claims, 6 Drawing Figures

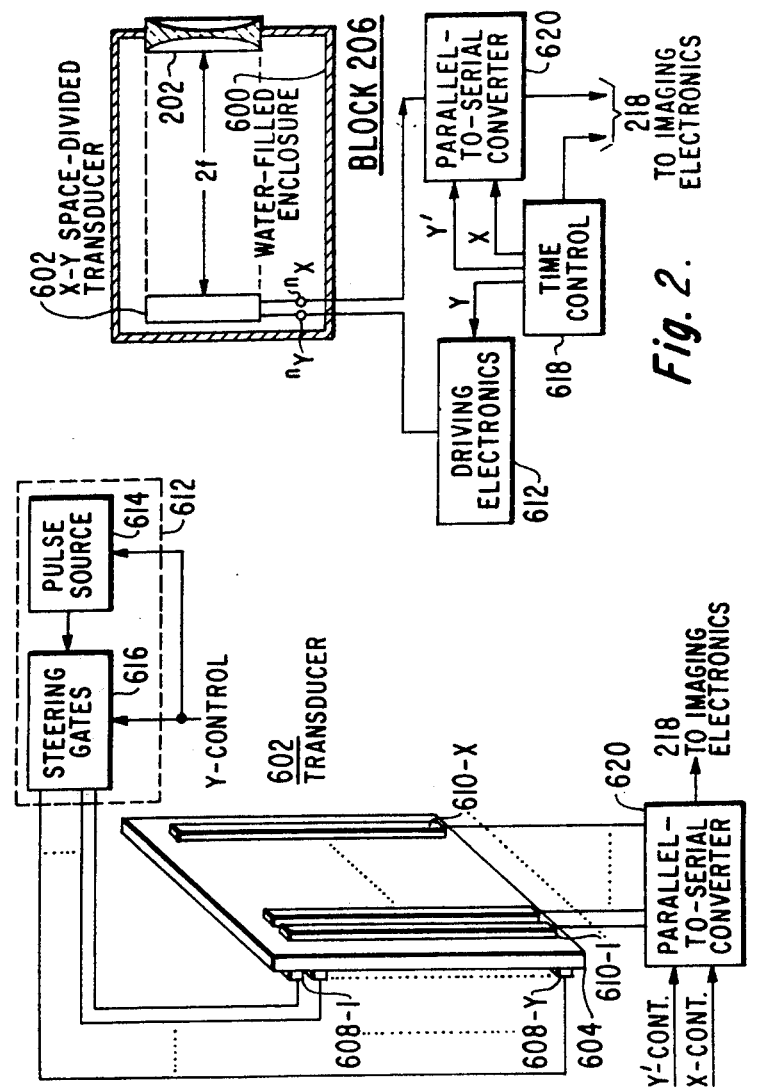

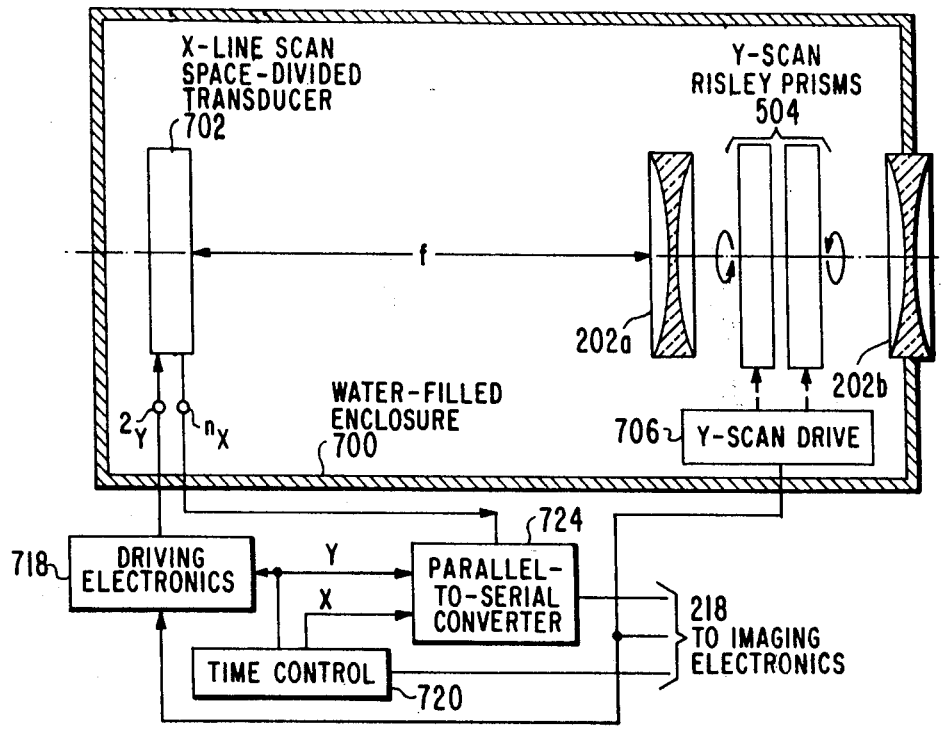
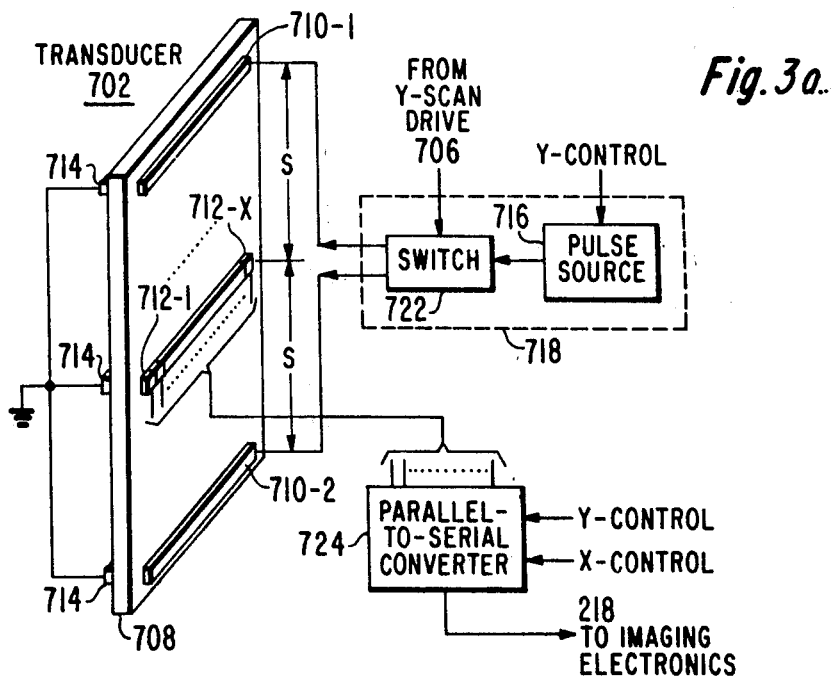

PULSE-ECHO ULTRASONIC-IMAGING DISPLAY SYSTEM

Reference should be made to the following U.S. Pat. applications, filed concurrently herewith and assigned to the same assignee as the present invention:

Ser. No. 766,564 — Mezrich & Koenig
Ser. No. 766,565 — Mezrich & Anderson
Ser. No. 766,527 — Mezrich
Ser. No. 766,526 — Mezrich & Avins The aforesaid U.S. Pat. application Ser. No. 766,564 Mezrich and Koenig, describes in detail a number of embodiments of a high resolution pulse-echo ultrasonic-imaging display system employing an acoustic focused device occupying a fixed aperture for both illuminating internal structure of a visually opaque object with a scanning focused beam of ultrasonic energy and for returning a reflected signal portion of the scanning focused beam passed therethrough or detection. The present application is directed to a certain one of these embodiments for providing real time scanning in a specific manner which inherently exhibits low parasitic shunting by a transducer which both generates the ultrasonic energy and detects the reflected signal portion.

Figure 1:
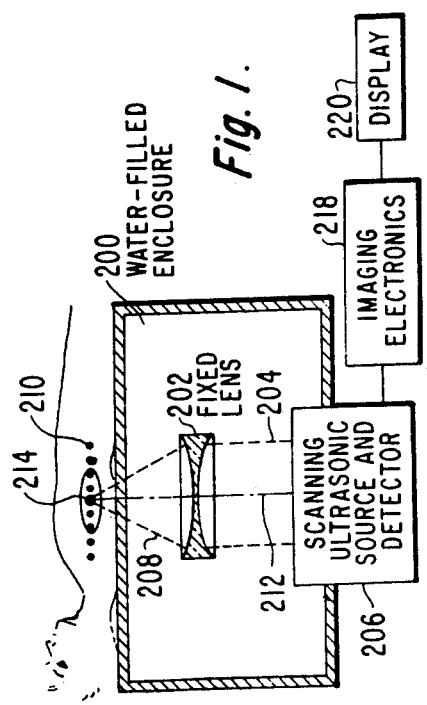

In the drawings:

FIGS. 1 and 1a generically illustrate the type of pulse-echo ultrasonic-imaging system that may embody the present invention;

FIGS. 2 and 2a illustrate a first species of the scanning ultrasonic source and detector of FIG. 1; and FIGS. 3 and 3a illustrate a second species of the scanning of ultrasonic source and detector of FIG. 1;

FIGS. 1, 1a, 2, 2a, 3 and 3a of the present case correspond identically with respective FIGS. 2, 2a, 6a, 6b, 7a and 7b of the aforesaid U.S. patent application Ser. No. 766,564.

Referring now to FIGS. 1 and 1a, there is shown a human patient lying on water-filled table 200. Immersed within water-filled table 200 is fixed lens 202, which is illuminated by a substantially plane wavefront beam 204 of ultrasonic energy from scanning ultrasonic source and detector 206 disposed in spaced relationship with fixed lens 202.

The term "fixed" lens, as used herein, means that the effective position of the aperture of lens 202 remains substantially stationary with respect to the human patient lying on water-filled table 200 during an image scan. However, in order to select the particular soft tissue within the human patient to be imaged, the operating distance between lens 202 and the human patient may be adjusted, if desired, prior to an image scan, by either changing the height of the top of water-filled table 200 with respect to lens 202 or by changing the position of lens 202 with respect to the top of water-filled table 200, without departing from the above definition of "fixed" lens. Further, since the mere rotation of a circularly symmetrical lens about its own axis has no effect at all on the position of the lens aperture or the way the lens acts on ultrasonic energy transferred therethrough, such mere rotation of the lens about its own axis is to be construed as to be within the above definition of the term "fixed" lens. Fixed lens 202 transfers the ultrasonic energy in plane wavefront beam 204 incident thereon into converging beam 208, which focuses at a small spot of focal plane 210 of lens 202 (located within the body of the human patient).

FIG. 1 shows plane-wavefront illuminating beam 204 of ultrasonic energy at a point in its scan where its direction of travel is parallel to acoustic axis 212 of fixed lens 202. In this case, ultrasonic energy converging beam 208 emerging from fixed lens 202 focuses at a spot centered at focal point 214 in focal plane 210 of lens 202. However, as shown in FIG. 1a, when plane wavefront illuminating beam 204 is at a point in its scan where its direction of travel is angularly displaced by angle $\theta$ from acoustic axis 212 of lens 202, converging beam 208 emerging from lens 202 focuses at a spot centered at point 216 in focal plane 210 of lens 202. As shown in FIG. 1a, point 216 is linearly displaced by a distance d from focal point 214. As is known in the optical art, the relationship between the distance d and the angular displacement $\theta$ is given by the following equation:

$$d = f\theta, \tag{1}$$

where f is the focal distance of lens 202, as shown in FIG. 1a, and the maximum value of $\theta$ is sufficiently small (as is the case) to be substantially equal in radians to $\tan \theta$.

It will be noted from equation 1 that the value of d varies linearly with $\theta$. Further, as the value $\leftarrow$ varies during a scan, the position of the point, such as point 216, to which beam 208 converges remains in focal plane 210. This ensures a substantially flat-field image (neglecting the effect of any lens aberration).

Referring now to FIGS. 2 and 2a, there is shown a space-divided embodiment of scanning ultrasonic source and detector 206 for providing real-time scanning of the target area.

Lens 202 is incorporated into the front wall of water-filled enclosure 600. Immersed in water-filled enclosure 600 is X-Y space-divided transducer 602. Transducer 602 is preferably situated at a distance from lens 202 equal to twice its focal strength (2f), as indicated in FIG. 2, so that points on transducer 602 are imaged with unity magnification on a target area plane situated at a distance beyond lens 202 also equal to 2f. Similarly, points in the target area will be imaged with unity magnification at transducer 602. As shown in FIG. 2a, transducer 602 comprises piezoelectric plate 604 having a first set of driving line-section electrodes 608-1 . . . 608-y on the left surface thereof and a second set of sensing line-section electrodes 610-1 . . . 610-x on the right face thereof. As shown, the second set of electrodes is orthogonally oriented with respect to the first set of electrodes to thereby define (x · y) cross points therebetween. Each of these cross points corresponds to a sampling point of the target area. If, as has been assumed, x and y both have a value of 100, the total number of sampling points in the scan of the target area is 10,000.

Driving electronics 612 for energizing transducer 602 comprises pulse source 614 and steering gate 616. More specifically, under the control of Y signals from time control 618, steering gate 616 operates as a commutator to selectively supply successive exploratory pulses in sequence to each of driving electrodes 608-1 . . . 608-y, while simultaneously grounding all the non-selected remaining ones in this first set of electrodes. At the time an exploratory pulse is applied to driving electrodes 608-1 . . . 608-y, sensing electrodes 610-1 . . . 610-x are also grounded. This results in a narrow (e.g. 1 mm.) line beam of ultrasonic energy consisting of the energy launched from each of the cross-points of the then-selected one of driving electrodes 608-1 . . . 608-y.

Because each sampling point of the target area is imaged at a corresponding cross-point of the transducer in the arrangement of block 206 shown in FIGS. 2 and 2a, the round-trip travel time between the transmission of an exploratory pulse and the receipt of an echo from the target area in response thereto is twice that of the previously discussed embodiments of block 206. More specifically, if the target area is situated ten inches beyond lens 202 (i.e. $2f$ = 10 inches), as has been assumed, the total distance between transducer 602 and the target area is 20 inches. Therefore, the round trip travel time is in the order of 660 $\mu$s (assuming a velocity of 1500 m/s for the ultrasonic energy in the propagating medium). Y control signals are applied to pulse source 614 in steering gates 616 at the beginning of a period equal to or slightly greater than the round-trip travel time (660 $\mu$s) to cause each respective driving electrode 608-1 . . . 608-y to launch an exploratory pulse of ultrasonic energy in consecutive order at substantially 660 $\mu$s intervals.

Parallel-to-serial converter 620, which includes a set of x storage elements, a set of input gates under the control of Y' signals from time control 618 for applying the signals sensed by the sensing electrodes 610-1 . . . 610-x to the corresponding storage elements at or near the end of each Y (660 $\mu$s) period, and a steer-out circuit under the control of signals from time control 618 for sequentially reading out all the stored signals on the set of storage elements during the following y period to thereby apply a serial stream of x (e.g. 100) sample point signals to imaging electronics 218 during that Y period. Time control 618 also supplies scan sync signals to imaging electronics 218. Thus, the scan of the entire target area takes (y + 1) Y periods or, in the assumed example, 66.66 ms. This is or real-time frame rate of 15 scans of the target area per second.

At the end of any Y period, while parallel-to-serial converter 620 is sampling the echoes returned from the target area in response to the exploratory pulse transmitted from a particular one of driving line-section electrodes at the beginning of that Y period, it may be desirable for steering gate 616 to momentarily disconnect electrodes 608-1 . . . 608-y (i.e. allow electrode 608-1 . . . 608-y to float), in order to reduce the effective shunting parasitic load impedance between sensing electrodes 610-1 . . . 610-x and ground. This shunting load impedance tends to reduce the effective sensitivity and raise the effective signal-to-noise ratio of the sensed signals forwarded by sensing electrodes 610-1 . . . 610-x to the storage elements of parallel-to-serial-converter 620. In any event, all other things being equal, the greater the number of x-y cross-points, the greater is the effect of the shunting load impedance.

FIGS. 3 and 3a show an embodiment of scanning ultrasonic source and detector 206, which operationally is the functional equivalent of the embodiment shown in FIGS. 2 and 2a, but which inherently exhibits a much lower parasitic shunting load impedance.

Referring to FIG. 3, immersed in water-filled enclosure 700 are X line-scan space-divided transducer 702 and Y-scan Risley prisms 704 coupled to Y-scan drive 706. Sample points of the target area are imaged at corresponding points of transducer 702 by a lens system composed of two spaced lenses 202a and 202b, situated, as shown, on either side of Y-scan Risley prisms 704. This imaging results from the fact that the lens 202b, which is incorporated in the front wall of water-filled enclosure 700, has its focal plane situated in coincidence with the target area, and transducer 702 is located in the focal plane of lens 202a. The use of a two-lens system to provide imaging of the sample points of the target area on transducer 702 is to be preferred in the arrangement of FIG. 3 to the single lens approach used in FIG. 2 because the two-lens approach ensures less distortion because the Y-scan Risley prisms are illuminated with paraxial plane-wave acoustic energy, rather than spherical wave energy from a linearly-scanned point source.

Referring now to FIG. 3a, transducer 702 comprises piezoelectric plate 708 having two driving line-section electrodes 710-1 and 710-2 mounted on the right face thereof. Halfway between driving line-section electrode 710-1 and 701-2, at a distance "s" from each, is a linear array of individual sensing electrodes 712-1 . . . 712-x. Mounted on the left face of piezoelectric plate 708, in corresponding relationship with each of driving line-section electrodes 710-1 and 710-2 and the linear array of sensing electrodes 712-1 . . . 712x are grounded line-section electrodes 714, as shown. Pulse source 716 of driving electronics 718, in response to Y control signals from time control 720, applies a series of exploratory pulses to a selected one of driving electrodes 710-1 and 710-2 through switch 722 at a repetition rate which is substantially equal to the round trip travel time between the transmission of an exploratory pulse and a receipt of an echo from the target area response thereto (e.g. 660 $\mu$m). Switch 722 selects the one of the driving electrodes 710-1 and 710-2 which an exploratory pulse is forwarded in response to a control signal from Y-scan drive 706 applied thereto.

Y-scan Risley prisms 704 are continuously rotating during the time an exploratory-pulse is traveling toward the target and during the time that an echo therefrom is traveling back toward transducer 702. Therefore, an echo responsive to an exploratory pulse launched from a selected one of driving electrodes 710-1 and 710-2 does not return to that selected driving electrode, but is incrementally deflected in the Y direction by a given distance which is determined by the speed of rotation of Y-scan Risley prisms 704 and the round-trip travel time to the target area. The spacing distance between the linear array of sensing electrode 712-1 . . . 712-x and either one of the driving electrode 710-1 and 710-2 is chosen to be equal to this given distance. Furthermore, during a first half of each cycle of Y-scan Risley prisms 704, a beam of acoustic energy passing therethrough is deflected in the Y-direction from the top-to-bottom. However, during the remaining half of each cycle of location of Y-scan Risley prisms 704, a beam of acoustic energy passing there through is deflected in the Y-direction from bottom-to-top. The control signal applied to switch 722 from Y-scan drive 706 causes exploratory pulses to be forwarded to driving electrode 710-1 and driving electrode 710-2 to be grounded during the half-cycle of rotation of Y-scan Risley prisms 704 when the acoustic beam is being deflected from top-to-bottom. Similarly, exploratory pulses are applied to driving electrode 710-2 and driving electrode 710-1 is grounded by switch 722 during those half-cycles of Risley prisms 704, during which the acoustic beam is deflected from bottom-to-top. In either case, returning echoes from the target area are incident on the linear-array of sensing electrode 712-1 . . . 712-x.

Assuming that the cycle period of Y-scan Risley prisms 704 is not exactly equal to an even integral multiple of the repetition period of the exploratory pulses, a different set of X-lines of the target area will be sampled during consecutive half-cycles of rotation of Risley prisms 704. That is, an inter-laced raster scan of the target area is achieved.

Parallel-to-serial converter 724, which is structurally and functionally identical to parallel-to-serial converter 620, described above, the end of teach Y period (i.e. exploratory pulse repetition period) samples in parallel and stores all the line of target area echo signals then being received by snesing electrode 712-1 ... 712-x, and then converts the stored signals into a corresponding serial stream during the following Y periods. What is claimed is:

1. In apparatus for use in an ultrasonic pulse-echo system capable of displaying an image of certain internal structure of a visually opaque object being scanned with ultrasonic wave energy, said apparatus including an acoustic focusing device occupying a given aperture which remains substantially fixed in position with respect to said object while said object is being scanned, and ultrasonic beam forming means including transducer means generating successive pulses of ultrasonic wave energy and beam scanning means for illuminating said certain internal structure through said focusing device with a scanning focused beam of said pulsed ultrasonic wave energy, said transducer means being situated remotely from both said focusing device and from said internal structure for receiving and detecting a signal portion of said focused beam reflected from said certain internal structure and returned through said focusing device to said transducer means after a time delay proportional to the distance between said remotely situated transducer means and internal structure; the improvement:

wherein said transducer means is situated in a given region in which said object is imaged by said focusing device, and said transducer means includes first and second parallel wave energy generating electrodes extending linearly in a first direction and spaced from each other by a certain distance, and a linear array of image-spot detecting electrodes extending in said first direction and situated halfway between said first and second electrodes, whereby all said detecting electrodes are the same given distance from said first electrode as they are from said second electrode, and wherein said ultrasonic beam focusing means includes a pair of Risley prisms counter-rotating at a predetermined rate for linearly scanning said focused beam in second direction orthogonal to said first direction, said predetermined rate being related to said given distance such that during a certain half-cycle of rotation of said Risley prisms said detection electrodes each receive a signal portion of said focused beam generated by said first electrode and during the remaining half-cycle of rotation of said Risley prisms said detecting electrodes each receive a signal portion of said focused beam generated by said second electrode.

2. The apparatus defined in claim 1, wherein said ultrasonic beam forming means further includes means synchronized with the rotation of said Risley prisms for supplying driving pulses at a given repetition period no less than said time delay to said first electrode during said certain one-half cycle of rotation of said Risley prisms and to said second electrode during said remaining half-cycle of rotation of Risley prisms.

3. The apparatus defined in claim 2, wherein said ultrasonic beam forming means further includes respective sample storage means selectively coupled in parallel to respective ones of said detecting electrodes when signal portions of said focused beam are being received and detected, and second means for serially reading out all said respective stored samples in a time period immediately following the storing thereof, said time period being no greater than said repetition period.

* * * * *

UNITED STATES PATENT AND TRADEMARK OFFICE
CERTIFICATE OF CORRECTION

PATENT NO. : 4,131,024
DATED : December 26, 1978
INVENTOR(S) : Reuben Saul Mezrich et al.

It is certified that error appears in the above-identified patent and that said Letters Patent is hereby corrected as shown below:

Column 2, line 27, "←" should read --$\theta$--

Signed and Sealed this

Seventeenth Day of April 1979

[SEAL]

Attest:

RUTH C. MASON
Attesting Officer

DONALD W. BANNER
Commissioner of Patents and Trademarks